Figure 1:
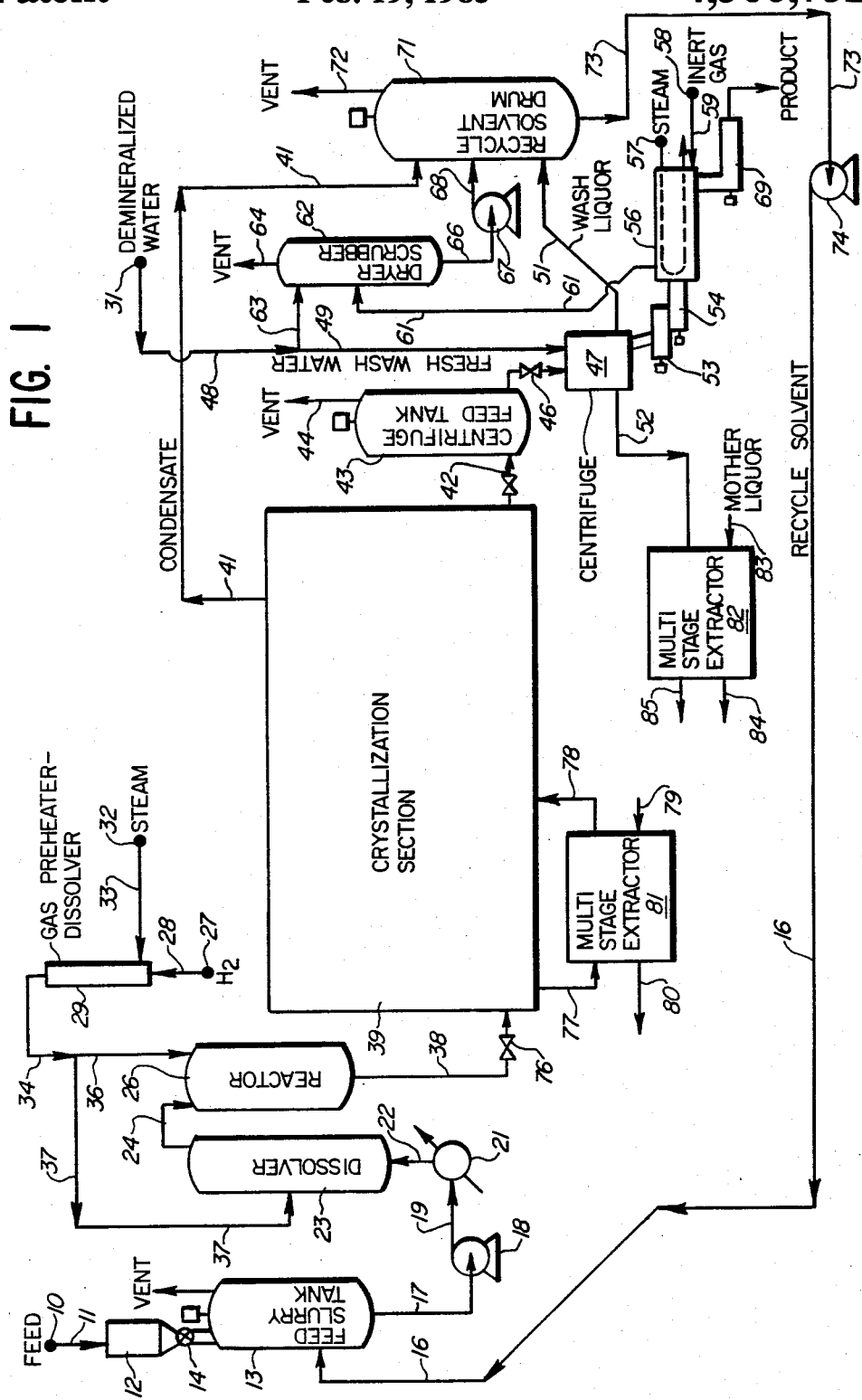

United States Patent [19]

Petty-Weeks et al.

[11] Patent Number: 4,500,732
[45] Date of Patent: Feb. 19, 1985

[54] PROCESS FOR REMOVAL AND RECYCLE OF P-TOLUIC ACID FROM TEREPHTHALIC ACID CRYSTALLIZER SOLVENT

[75] Inventors: Bruce C. Petty-Weeks; Martin A. Zeitlin, both of Naperville, Ill.

[73] Assignee: Standard Oil Company (Indiana), Chicago, Ill.

[21] Appl. No.: 532,461

[22] Filed: Sep. 15, 1983

[51] Int. Cl.$^3$ ............................................. C07C 51/43
[52] U.S. Cl. ................................... 562/486; 562/412; 562/414; 562/485
[58] Field of Search ................ 562/485, 486, 412, 414

[56] References Cited

U.S. PATENT DOCUMENTS

| | | | |
|---|---|---|---|
| 2,794,832 | 6/1957 | Rietema | 562/486 |
| 2,811,548 | 10/1957 | Ham et al. | 562/486 X |
| 2,838,565 | 6/1958 | Heath et al. | 562/486 X |
| 3,452,088 | 6/1969 | Olsen et al. | 562/486 |
| 3,497,552 | 2/1970 | Olsen | 562/486 |

*Primary Examiner*—Natalie Trousof
*Assistant Examiner*—Vera C. Clarke
*Attorney, Agent, or Firm*—Gunar J. Blumberg; William T. McClain; William H. Magidson

[57] ABSTRACT

A process for the removal of para-toluic acid from purified terephthalic acid is disclosed. This process comprises extracting the para-toluic acid with paraxylene from the aqueous terephthalic acid-water phase and recycling the para-toluic acid and paraxylene to the paraxylene oxidation reactor. The process improves the overall yield of purified terephthalic acid recovered. Purified terephthalic acid is used as a basic raw material in the manufacture of polyester fibers and films.

7 Claims, 1 Drawing Figure

PROCESS FOR REMOVAL AND RECYCLE OF P-TOLUIC ACID FROM TEREPHTHALIC ACID CRYSTALLIZER SOLVENT

FIELD OF THE INVENTION

This invention relates to a process for the removal of para-toluic acid from terephthalic acid crystallizer solvent and to the recycle of the paraxylene containing extracted p-toluic acid to the paraxylene oxidation reactor.

BACKGROUND OF THE INVENTION

Terephthalic acid is used in large quantities as a starting material for the preparation of polyester fibers such as linear polyalkylene terephthalates. These polyesters can be prepared quite conveniently by, for example, direct condensation of ethylene glycol with terephthalic acid. In such processes the terephthalic acid used in fiber production must be of exceptionally high purity. However, terephthalic acid prepared by, for example, the oxidation of p-xylene contains oxidation intermediates as impurities. These intermediates must be removed from the acid to obtain a material suitable for use in making polyester fibers. A number of methods have been employed for purifying terephthalic acid by chemical or physical treatment to obtain an acid suitable for fiber production. For example, Canadian Pat. No. 768,189 discloses isolating pure terephthalic acid from an oxidation mixture by heating the oxidate at 210° to 280° C. for about ½ to 5 hours and recovering the purified terephthalic acid. Furthermore, p-xylene has been used to remove impurities from terephthalic acid but these methods have been digestion procedures with all their attentant disadvantages.

Other references of interest include U.S. Pat. Nos. 3,624,145; 3,546,285; 3,584,039 and 3,850,983. None of these references relate to the removal of the para-toluic acid with paraxylene while the terephthalic acid is in a water slurry during the crystallization step in the process for purifying terephthalic acid by hydrogenation under pressure in the presence of a metal catalyst. Most of the prior art processes are directed to the removal of 4-carboxybenzaldehyde and not to the removal of para-toluic acid.

Process of the invention is conducted at elevated temperature and pressure while the terephthalic acid is dissolved in water. By reason of its low solubility in water, terephthalic acid requires either large volumes of water or high temperatures in order for the desired terephthalic acid production quantity to be put into solution. For reasons of economic equipment design and process operation, it is therefore desirable to conduct the process within the range of about 392° to about 700° F., although lower or higher temperatures may be used in particular circumstances. The most advantageous temperature range is about 440°–575° F., e.g., 464°–550° F. The quantity of water needed to dissolve the terephthalic acid at various temperatures may be estimated from the table below:

TABLE 1

| Terephthalic acid, g/100 g, H$_2$O | Temperature, °F. for solution |
| --- | --- |
| 1 | 365 |
| 5 | 401 |
| 10 | 468 |
| 20 | 498 |

TABLE 1-continued

| Terephthalic acid, g/100 g. H$_2$O | Temperature, °F. for solution |
| --- | --- |
| 30 | 522 |

For the purification of crude terephthalic acid, aqueous solution temperatures in the range of 450° to 600° F. are preferred because these solutions carry more than 5 pounds of the acid per 100 pounds of water.

Pressure conditions for the process depend upon the temperature at which this process is conducted. Since the temperature at which significant amounts of the impure terephthalic acid may be dissolved in water are substantially above the normal boiling point of water, and since the hydrogenation section is to be carried out with the solvent in the liquid phase, the pressure will necessarily be substantially above atmospheric pressure.

It is advantageous to trickle the liquid solution of the terephthalic acid through a bed of the catalyst because lower hydrogen partial pressure or hydrogen driving force is required than is required when the catalyst bed is operated liquid full. Either a static hydrogen atmosphere or a flow, concurrent or countercurrent, of hydrogen through the catalyst chamber may be maintained. Lower hydrogen partial pressures are required for the trickle or percolation method of conducting the hydrogenation section because there is provided a thin film of the aqueous solution of the impure terephthalic acid on the catalyst particles and thus a lower hydrogen driving force is needed for the hydrogen to dissolve and diffuse through the thin liquid layer and reach the catalyst. For such percolation method of conducting the hydrogenation a continuous flow or atmosphere of hydrogen is not essential. However, for maximum hydrogenation rates it is beneficial to dissolve at least some hydrogen into the solution, conveniently in the acid dissolver, prior to contacting it with the catalyst. Hydrogen may be intermittently introduced into the bed of extended catalyst during the continuous introduction of the aqueous solution of impure terephthalic acid. The minimum of hydrogen to be introduced intermittently is, of course, an amount of hydrogen in excess of that required for reduction of the dissolved impurity so that adsorption of the excess hydrogen in the porous catalyst support can be simultaneously accomplished. Very little hydrogen is consumed by the purification process.

It is particularly advantageous to impose on the aqueous solution being treated a pressure above the pressure required to maintain a liquid phase of the aqueous solution of impure terephthalic acid and dissolved hydrogen. This additional pressure prevents premature crystallization of the acid due to minor process pressure variations causing vaporization of some of the solvent. This is readily accomplished by use of an inert, non-condensable gas, such as nitrogen. By "inert" gas is meant that gas which is not reactive with the terephthalic acid or the hydrogen or solvent. Nitrogen is a convenient inert gas. An additional benefit accruing from the use of nitrogen is that the dilution of the hydrogen introduced into the process provides low partial pressure of hydrogen to minimize over-hydrogenaton, such as, for example, saturation of aromatic nuclei.

Hydrogen treating time, or space velocity, will depend on the initial terephthalic acid purity, that is, the amount of impurity to be reduced, on the desired fiber-grade specifications imposed on the purified terephthalic acid, and on other conditions of the hydrogenation, such as, for example, catalyst activity. Ordinarily, a treating time, i.e. contact time with the catalyst, within the range of about 0.001 to about 10 hours, advantageously about 0.01 to 2 hours, will suffice for most operations. Although treating time is not a critical variable, it must be taken into consideration with regard to the aforementioned severe hydrogenation and its side effects.

The hydrogenation catalyst required, for the process of this invention, to convert the aldehyde carbonyl group on the 4-carboxybenzaldehyde (4-CBA) to para-toluic acid and to destroy, or otherwise render innocuous, other impurities present (e.g. those of benzil and fluorenone structure) in the feed terephthalic acid are preferably a Group VIII noble metal, preferably platinum and/or palladium, supported on adsorbent, high surface area charcoal. A wide variety of catalysts have been found efficacious, and while carbon-supported noble metals are outstanding, reference may be made to any of the standard texts on hydrogenation or catalysts for alternative materials which are catalytically effective under aqueous phase hydrogenation conditions. It must be kept in mind, however, that the catalyst used must be one which is useful for effecting the hydrogenation under mild hydrogenation conditions as defined herein. Numerous catalysts are listed, for example, in Kirk and Othmer's *Encyclopedia of Chemical Technology* (Interscience), particularly the chapters on Hydrogenation and Catalysts; Emmett's *Catalysis*, (Reinhold), particularly Volumes IV and I on Hydrogenaton; Lohse's *Catalytic Chemistry* (Chemical Publishing Company), particularly the sections on Group VIII metal Catalysts; and such U.S. patents as U.S. Pat. Nos. 2,070,770 and 2,105,664. Illustrative catalysts include the Group VIII Nobel Metals Ruthenium, Rhodium, Palladium, Osmium, Iridium, and Platinum, advantageously extended on a support, such as activated carbon, e.g., adsorbent charcoal. Advantageously, noble metal contents in the range of about 0.05–0.5 weight percent may be used, with about 0.1–0.3 weight percent being the preferred noble metal content for use in trickle beds of catalyst. The higher noble metal contents tend to produce overhydrogenation while the lesser amounts suffer some loss in hydrogenation activity as compared with catalysts of the preferred noble metal content.

The adsorbent charcoal support for the noble metal may be any such support which has sufficient mechanical strength and surface area. It has been found that palladium-charcoal catalysts having a palladium content in the preferred range of 0.1–0.3 weight percent and also having a very high surface area in the range of about 1000–3000 square meters per gram of catalyst are particularly well suited for use in the present invention.

The hydrogen treated solution is filtered to remove any suspended solids, such as catalyst support fines and extraneous materials, of about 5 microns and larger in size. The purified acid is then recovered from the filtered solution. Crystallization is a convenient and preferred method for recovering the purified acid. Either batch or continuous crystallization may be employed in the crystallization section. Crystallized acid is recovered by centrifuging, during which further purification is effected by washing the centrifuge cake. The crystals are dried in a rotary kiln to a moisture content below about 1 wt. percent, preferably about 0.02–0.06 wt. percent, to prevent caking during subsequent storage and shipping.

Purified terephthalic acid obtained from the oxidation of p-xylene with molecular oxygen and reduction by hydrogenation contains certain impurities, primarily para-toluic acid, and amounts of other partial oxidation products that are also extremely difficult to remove. According to the present invention, a solution of purified terephthalic acid containing a weight ratio of acid to water of from about 5:100 to about 1:1, and preferably from about 1:5 to about 1:1, is mixed with a paraxylene liquid thereby forming a two-phase system of an aqueous phase containing purified terephthalic acid and an organic phase containing para-toluic acid and paraxylene. The paraxylene is added in an amount to produce a ratio of aqueous phase to organic phase of from about 1:1 to about 50:1, preferably from about 6:1 to about 10:1, separating the aqueous phase from the organic phase containing para-toluic acid, from the aqueous phase containing purified terephthalic acid, and then recovering purified terephthalic acid from the aqueous phase and recycling the para-toluic acid and paraxylene to the paraxylene oxidation reactor. Important features for the successful operation of this process are the weight ratio of purified terephthalic acid to water, the ratio of aqueous to organic phase, and the temperature maintained during extraction of the impurities. The process must be conducted under such conditions that impurities are extracted from an aqueous solution of terephthalic acid as contrasted to removal of impurities from solid terephthalic acid, i.e., digestion procedures.

The primary constituent of the organic phase that solvates the impurities in the liquid-liquid extraction process is paraxylene. The preferred extract is paraxylene since it can readily be recycled to the paraxylene oxidation reactor with para-toluic acid. The water-immiscible liquid paraxylene and the aqueous solution of terephthalic acid, when mixed in a single vessel in a batch process, or a series of mixers arranged to effect a countercurrent type extraction, or a continuous countercurrent flow through a single column, form an aqueous phase and an organic phase at the temperature stated above. Initially, the aqueous phase contains primarily terephthalic acid and impurities, whereas the organic phase contains primarily the paraxylene that is inert to terephthalic acid. However, after mixing the aqueous phase and the organic phase, the paraxylene solvates and removes para-toluic acid from the aqueous solution of terephthalic acid. The amount of time for the paraxylene treatment depends upon the particular procedure used and, of course, the amounts of ingredients treated. In general, a multiple stage batch process, in which the organic phase and aqueous phase are mixed by mechanical agitation and allowed to settle, or a continuous process employing a series of mixers and settlers of the type used in concurrent or countercurrent extraction systems, requires about 1 to about 10 minutes, usually about 4 to about 5 minutes, from mixing until extraction is complete, purified terephthalic acid recovered and para-toluic acid paraxylene mixture is recycled.

After paraxylene has solvated and removed the para-toluic acid from the aqueous solution of purified terephthalic acid, the organic phase contains paraxylene and para-toluic acid and the aqueous phase containing terephthalic acid is segregated, the organic phase is directed to the oxidation reactor, and the aqueous phase directed to the remaining crystallization or, alternatively, to centrifuges.

Turning now to the drawings, FIG. 1, is a simplified schematic flow plan of a preferred embodiment of the invention. It is to be understood that this embodiment is for the purpose of illustration and is not to be regarded as a limitation of the scope of the present invention.

In actual practice, the choice of the number of series-connected stirred crystallizaton zones, contained in the crystallization section using flash evaporation of water, is associated with the concentration of p-toluic acid based on terephthalic acid and not on the p-toluic acid concentration in the solution fed to any one zone, since crystallization of each incremental amount of terephthalic acid is substantially instantaneous, and not based on any rate dependent technique for effecting terephthalic acid crystallization. For such initially dissolved purified terephthalic acid, having 500–6000 ppm of p-toluic acid by weight based on terephthalic acid, the number of such flash evaporations of solvent in series, in general will not exceed a total of eight stirred crystallization zones.

By utilizing the improvements of this invention, and practicing them as shown in FIG. 1—which improvements comprise extracting the terephthalic acid slurry of its p-toluic acid content between two of the crystallization zones via line 77 in a multistage extractor 8 with paraxylene, and returning the extracted slurry via line 78 to the next crystallization zone—the number of crystallization zones can be reduced. Paraxylene is added to the multistage extractor 81 via line 79. Paraxylene, rich in p-toluic acid, is removed from the multistage extractor 81 via line 80 where it can be used as a feed to a conventional oxidation unit thereby increasing the traditional yield for that process.

As a second embodiment to this invention, mother liquor, traditionally withdrawn from the centrifuge and discarded via line 52, can be sent to a second multistage extractor 82 and extracted with paraxylene. Extracted mother liquor can be sent to a further treatment step or discarded via line 85. Paraxylene is added to multistage extractor 82 via line 83. Paraxylene, rich in p-toluic acid, is removed from the multistage extractor 82 via line 84 where it can be used as a feed to a conventional oxidation unit thereby increasing the traditional yield for that process or p-toluic acid can be recovered and sold.

The following is a further description of FIG. 1 showing the preferred process. In FIG. 1, dry crude terephthalic acid feed (e.g. containing 0.1 to 1.0 percent by weight 4-carboxybenzaldehyde) from source 10, such as, for example, a storage silo, is transferred via line 11 into crude terephthalic weight hopper 12. Crude terephthalic acid is fed from the weight hopper at a constant rate into the feed slurry tank 13 by the crude terephthalic feeder 14 which suitably can be any solids transfer feeder such as, for example, a Star feeder. The crude terephthalic feeder 14 sets the nominal feed rate of the process. Recycled water from line 16 is added to feed slurry tank 13 on flow control to provide a slurry concentration of crude terephthalic acid in water of approximately 15–35 weight percent, preferably about 20–30 weight percent, and in this example about 23.1 weight percent total solids. Demineralized water is preferred as solvent water. Slurry hold-up, in feed slurry tank 13 of about 45 minutes at normal level, is sufficient to dampen out fluctuations in the terephthalic acid and water feed rates to the tank. The temperature in feed slurry tank 13 is maintained at a temperature in the range of about 100°–300° F., preferably about 200° F. and the pressure is conveniently near atmospheric, at temperatures below the boiling point of water. Feed slurry tank 13 is provided with an agitator to contact the solid crude terephthalic acid and the recycled water in order to maintain a uniform slurry.

Slurry is withdrawn from feed slurry tank 13 via line 17 and transferred via high-pressure pump 18 via line 19 through preheater 21. Preheater 21 is conveniently a shell-and-tube exchanger with one or two tube pass. Normally the tube-side velocity of the slurry feed is sufficient to keep the slurry in suspension. Suitable preheater outlet conditions of temperature and pressure are about 525° to about 530° F. and about 985 p.s.i.a., respectively. The preheater slurry is passed via line 22 into dissolver 23.

The reactor feed stream is passed up-flow through the dissolver 23 which provides a residence time of approximately 20 minutes. A clear solution of terephthalic acid in water overflows from the dissolver 23 via line 24 to the hydrogenation reactor 26. This solution, when formed from a slurry of approximately 23.1 weight percent solids, contains about 30 pounds of crude terephthalic acid per 100 pounds of water at about 525° to about 530° F. and 985 p.s.i.a. The precipitation (crstallization) point for this solution is about 522° F.

Crude terephthalic acid solution from line 24 flows continuously into the hydrogenation reactor 26. The bed is supported by a screen about equivalent to 8-gauge Tyler mesh.

Hydrogen from source 27, is passed via line 28 into gas preheater-dissolver 29. Steam and hot condensate from source 32 is also passed via line 33 into gas preheater-dissolver 29 wherein the hydrogen-containing gas is heated to reaction temperature. The stream from the preheater-dissolver is passed via lines 34 and 36 into the top section of the reactor 26 so that hydrogen is dissolved in the solution and thus is readily available to effect hydrogenation upon contact with the catalyst in the center section of reactor 26.

Since the terephthalic acid solution is highly corrosive at reactor effluent temperature, careful selection of suitable corrosion resistant elements is required.

Reactor effluent is passed via line 38 and inlet valve 76 to crystallization section 39. In the crystallization section, water is removed from the hot terephthalic acid solution by high-rate evaporative cooling. As a result of both the cooling and the solvent removal, terephthalic acid crystallizes from solution. Evaporated water is condensed and the condensate is withdrawn from the crystallization section and passed via line 41 into recycle solvent drum 71. The slurry of terephthalic acid crystals resulting from the crystallization is withdrawn from the crystallization section via line 42 and passed into centrifuge feed tank 43 which is vented to the atmosphere by line 44. The centrifuge feed tank 43 is provided with an agitator to maintain the slurry of terephthalic acid crystals in suspension. The terephthalic acid slurry is passed from the centrifuge feed tank 43 via valved line 46 into one or more centrifuges 47 wherein the crystals are separated from the mother liquor and the crystals washed with fresh demineralized wash water obtained from source 31 via lines 48 and 49. Wash water from the centrifuge is passed via line 51 into the recycle solvent drum 71. Mother liquor is withdrawn from the centrifuge and discarded via line 52. Purified terephthalic acid crystals from the centrifuge 47 are withdrawn and fed via auger feeders 53 and 54 into rotary kiln crystal dryer 56 which is heated by steam from source 57. Inert gas, such as nitrogen, from source 58 may be passed via line 59 into and through drying kiln 56 to assist in removing moisture from the terephthalic acid crystals. The product is dried to a moisture content of about 0.05 weight percent water. Inert gas and water vapor containing some terephthalic acid fines are withdrawn from the kiln 56 and passed via line 61 into dryer-scrubber 62 wherein the gases are washed countercurrently by a stream of fresh demineralized water. The water is introduced to the dryer-scrubber 62 from source 31 via lines 48 and 63 and descends countercurrently to the rising gas stream removing terephthalic acid fines from the gases which are vented from the scrubber via line 64. Water containing terephthalic acid fines is withdrawn from the dryer-scrubber 62 and passed via lines 66, pump 67 and line 68 into the recycle solvent drum 71. The solvent drum is vented to the atmosphere via line 72. An agitator is provided within the solvent recycle drum 71 in order to maintain undissolved particles of terephthalic acid, primarily from scrubber 62, in suspension. Recycle solvent water is withdrawn from the recycle solvent drum 71 and passed via line 73, pump 74, and line 16 into the feed slurry tank 13. Dried purified terephthalic acid product is withdrawn from the drying kiln 56 and passed via conveyor 69 to storage.

The following examples further illustrate the invention but are not to be considered as limiting the teachings of the invention.

EXAMPLE 1

A mixture of 100 g water, 86.6 g p-xylene and 1.715 g of p-toluic acid was stirred rapidly at 96° C. for 5 min. Stirring was stopped and the two phases allowed to separate. Both the p-xylene and aqueous phases were analyzed by High Pressure-LC and found to contain 1.86 and 0.111 wt % p-toluic acid respectively. The distribution coefficient is 16.8.

$$\frac{[\text{p-toluic acid}]\text{p-xylene}}{[\text{p-toluic acid}]\text{water}}$$

The results are set forth in Table 2.

TABLE 2 p-Toluic Acid Distribution between p-Xylene and $H_2O$ at 96° C.

| SAMPLE | Wt % p-toluic acid Px | Wt % p-toluic acid $H_2O$ | Distribution Coefficients Concentration in Px / Concentration in Water |
|---|---|---|---|
| 1 | .7104 | .0676 | 10.5 |
| 2 | 1.863 | .1110 | 16.8 |
| 3 | .0802 | .0143 | 5.6 |
| 4 | .0473 | .0082 | 5.8 |
| 5 | .2450 | .0353 | 6.9 |

| | | Mass Balance (g) | | |
|---|---|---|---|---|
| 1 | .615 | .0676 | .6826/.6383 | 107% |
| 2 | 1.614 | .111 | 1.725/1.7146 | 101% |
| 3 | .06945 | .0143 | 0.08375/.0844 | 99% |
| 4 | .0496 | .0082 | 0.04916/.0500 | 98% |
| 5 | .06370 | .0353 | .0990/.0804 | 123% |

We claim:

1. A continuous process for removal of p-toluic acid from a liquid water solution substantially saturated with terephthalic acid wherein the terephthalic acid content in water is in the range of about 5 to about 35 weight percent at a temperature of about 400° to about 550° F. and wherein the water solution comprises about 500 to about 6,000 ppm of p-toluic acid said process comprising, after continuously charging such liquid water solution to the first of two or more series-connected flash solvent evaporators wherein each crystallization zone is operated at a successively lower temperature with at least the last zones operated at a temperature within and below the range of about 375° F. to about 300° F., crystallizing decreasing proportions of originally dissolved terephthalic acid, extracting the terephthalic acid of its p-toluic acid between any two continuous crystallization zones with paraxylene, removing the flash evaporated solvent from each zone while retaining temperature of recovery of terephthalic acid product the same as the temperature of the last zone and removing the paraxylene containing p-toluic acid from a multistage extraction zone.

2. The process of claim 1 wherein the number of series-connected zones is about 3 to about 6.

3. The process of claim 1 wherein the extraction of p-toluic acid with paraxylene takes place after one of the first three crystallization zones.

4. The process of claim 3 wherein the temperature of the last zone is in the range of about 340° to about 300° F.

5. The process of claim 1 wherein mother liquor is sent to a second multistage extraction zone and extracted with paraxylene and recovered.

6. A process for the removal of p-toluic acid from terephthalic acid which process comprises contacting a water solution of terephthalic acid containing the weight ratio of terephthalic acid to water of about 5:100 to about 1:1 with paraxylene thereby forming a two-phase system of (a) a water phase containing terephthalic acid and (b) an organic phase containing paraxylene and p-toluic acid extracted from the terephthalic acid, the paraxylene is added in an amount sufficient to produce a ratio of aqueous phase to organic phase from about 1:1 to about 50:1.

7. The process of claim 6 wherein the weight ratio of terephthalic acid to water is about 1:5 to about 1:1.

* * * * *